(12) United States Patent
Adachi et al.

(10) Patent No.: US 11,234,730 B2
(45) Date of Patent: Feb. 1, 2022

(54) ULTRASONIC PROBE CONTROL METHOD AND COMPUTER-READABLE STORAGE MEDIUM HOLDING PROGRAM

(71) Applicant: SOCIONEXT INC., Kanagawa (JP)

(72) Inventors: Naoto Adachi, Yokohama (JP); Masaya Tamamura, Yokohama (JP); Amane Inoue, Yokohama (JP)

(73) Assignee: SOCIONEXT INC., Yokohama (JP)

( * ) Notice: Subject to any disclaimer, the term of this patent is extended or adjusted under 35 U.S.C. 154(b) by 326 days.

(21) Appl. No.: 16/113,373

(22) Filed: Aug. 27, 2018

(65) Prior Publication Data

US 2018/0360488 A1 Dec. 20, 2018

Related U.S. Application Data

(63) Continuation of application No. PCT/JP2016/062130, filed on Apr. 15, 2016.

(51) Int. Cl.
*A61B 8/14* (2006.01)
*A61B 17/34* (2006.01)
(Continued)

(52) U.S. Cl.
CPC ........ *A61B 17/3403* (2013.01); *A61B 8/0841* (2013.01); *A61B 8/463* (2013.01);
(Continued)

(58) Field of Classification Search
CPC ........ A61B 17/3403; A61B 2017/3413; A61B 8/0841; A61B 8/14; A61B 8/463; A61B 8/469; A61B 8/54; A61B 8/56
See application file for complete search history.

(56) References Cited

U.S. PATENT DOCUMENTS

2010/0160786 A1 6/2010 Nordgren et al.
2012/0078111 A1 3/2012 Tanabe et al.
(Continued)

FOREIGN PATENT DOCUMENTS

CN 204293264 U 6/2010
JP 2010-528697 A 8/2010
(Continued)

OTHER PUBLICATIONS

International Search Report issued in corresponding PCT Application No. PCT/JP2016/0621230 dated Jun. 7, 2016.
(Continued)

*Primary Examiner* — Mark D Remaly
(74) *Attorney, Agent, or Firm* — Arent Fox LLP

(57) ABSTRACT

A processor of a general-purpose terminal acquires position information indicating whether a biological body is punctured from a first side of an ultrasonic probe apparatus or a second side opposite to the first side and angle information indicating a puncture angle, where these items of information are entered on a touch panel of a display, transmits these items of information to the probe apparatus via a wireless communication circuit, acquires, via the communication circuit, image information generated and transmitted by the probe apparatus based on reflected waves obtained by transmitting ultrasonic waves into the biological body from the probe apparatus at a first angle based on the above information, superimposes a puncture guide indicating a puncture path based on the above information on an ultrasonic image of the biological body or a puncture needle based on the image information, and displays a result of the superimposing on the display.

5 Claims, 14 Drawing Sheets

(51) Int. Cl.
*A61B 8/08* (2006.01)
*A61B 8/00* (2006.01)

(52) U.S. Cl.
CPC .................. *A61B 8/54* (2013.01); *A61B 8/56* (2013.01); *A61B 8/14* (2013.01); *A61B 8/469* (2013.01); *A61B 2017/3413* (2013.01)

(56) References Cited

U.S. PATENT DOCUMENTS

| | | | |
|---|---|---|---|
| 2013/0102889 A1* | 4/2013 | Southard | A61B 8/0841 600/424 |
| 2013/0226001 A1 | 8/2013 | Steen et al. | |
| 2016/0081666 A1 | 3/2016 | Deguchi et al. | |
| 2016/0199134 A1* | 7/2016 | Brown | A61B 34/10 703/1 |

FOREIGN PATENT DOCUMENTS

| | | |
|---|---|---|
| JP | 2012-071014 A | 4/2012 |
| JP | 2013-172959 A | 9/2013 |
| JP | 2014-150936 A | 8/2014 |
| JP | 2014-212812 A | 11/2014 |
| KR | 2015013349 A | 11/2015 |
| WO | WO 2008/146203 A1 | 12/2008 |

OTHER PUBLICATIONS

International Search Report issued in corresponding PCT Application No. PCT/JP2016/062130 dated Jun. 7, 2016.

Chinese Office Action issued by the Chinese Patent Office in corresponding Chinese Application No. 201680084365.4, dated Oct. 19, 2020.

* cited by examiner

ULTRASONIC PROBE CONTROL METHOD AND COMPUTER-READABLE STORAGE MEDIUM HOLDING PROGRAM

CROSS-REFERENCE TO RELATED APPLICATION

This application is a continuation application of International Application PCT/JP2016/062130 filed on Apr. 15, 2016 which designated the U.S., the entire contents of which are incorporated herein by reference.

FIELD

The embodiments discussed herein relate to an ultrasonic probe control method and a computer-readable storage medium holding a program.

BACKGROUND

For example, when a puncture is performed for infusion of drug or removal of tissue, there are cases in which an ultrasonic diagnostic apparatus is used so that whether the puncture is correctly performed is checked with an ultrasonic image.

Generally, a needle used for a puncture is inserted diagonally from the surface of skin. To capture an ultrasonic image in which this needle is focused on, a probe of an ultrasonic diagnostic apparatus transmits ultrasonic waves to the needle perpendicularly to the direction of the insertion of the needle (this transmission could also be called "steer transmission") in such a manner that reception waves (reflected waves) are not attenuated. There is also a conventional method for supporting a puncture. In this method, a guideline indicating the insertion direction of a needle used for the puncture is displayed on a screen of an ultrasonic diagnostic apparatus.

See, for example, Japanese Laid-open Patent Publication No. 2014-212812, Japanese Laid-open Patent Publication No. 2012-71014, and Japanese National Publication of International Patent Application No. 2010-528697.

In many cases, when a user performs a puncture, the user holds a probe of an ultrasonic diagnostic apparatus in his or her hand. However, it is desirable that the user be able to perform the puncture with less stress. Namely, none of the conventional techniques sufficiently supports the user in performing the puncture. Therefore, there is demanded a technique that allows the user to be able to perform the puncture more easily.

SUMMARY

According to one aspect, there is provided an ultrasonic probe control method including: acquiring, by a processor of a general-purpose terminal apparatus, position information which indicates whether a biological body is punctured from a first side of an ultrasonic probe apparatus or a second side opposite to the first side and angle information which indicates a puncture angle, the position information and the angle information being entered on a touch panel of a display apparatus of the general-purpose terminal apparatus; transmitting, by the processor, the position information and the angle information to the ultrasonic probe apparatus via a wireless communication circuit of the general-purpose terminal apparatus; acquiring, by the processor, via the wireless communication circuit, first image information generated and transmitted by the ultrasonic probe apparatus based on a first reflected wave obtained by transmitting a first ultrasonic wave into the biological body from the ultrasonic probe apparatus at a first angle based on the position information and the angle information; and superimposing, by the processor, a puncture guide, which indicates a puncture path based on the position information and the angle information, on a first ultrasonic image of the biological body or a puncture needle based on the first image information and displaying a result of the superimposing on the display apparatus.

The object and advantages of the invention will be realized and attained by means of the elements and combinations particularly pointed out in the claims.

It is to be understood that both the foregoing general description and the following detailed description are exemplary and explanatory and are not restrictive of the invention.

DESCRIPTION OF EMBODIMENTS

Figure 1:
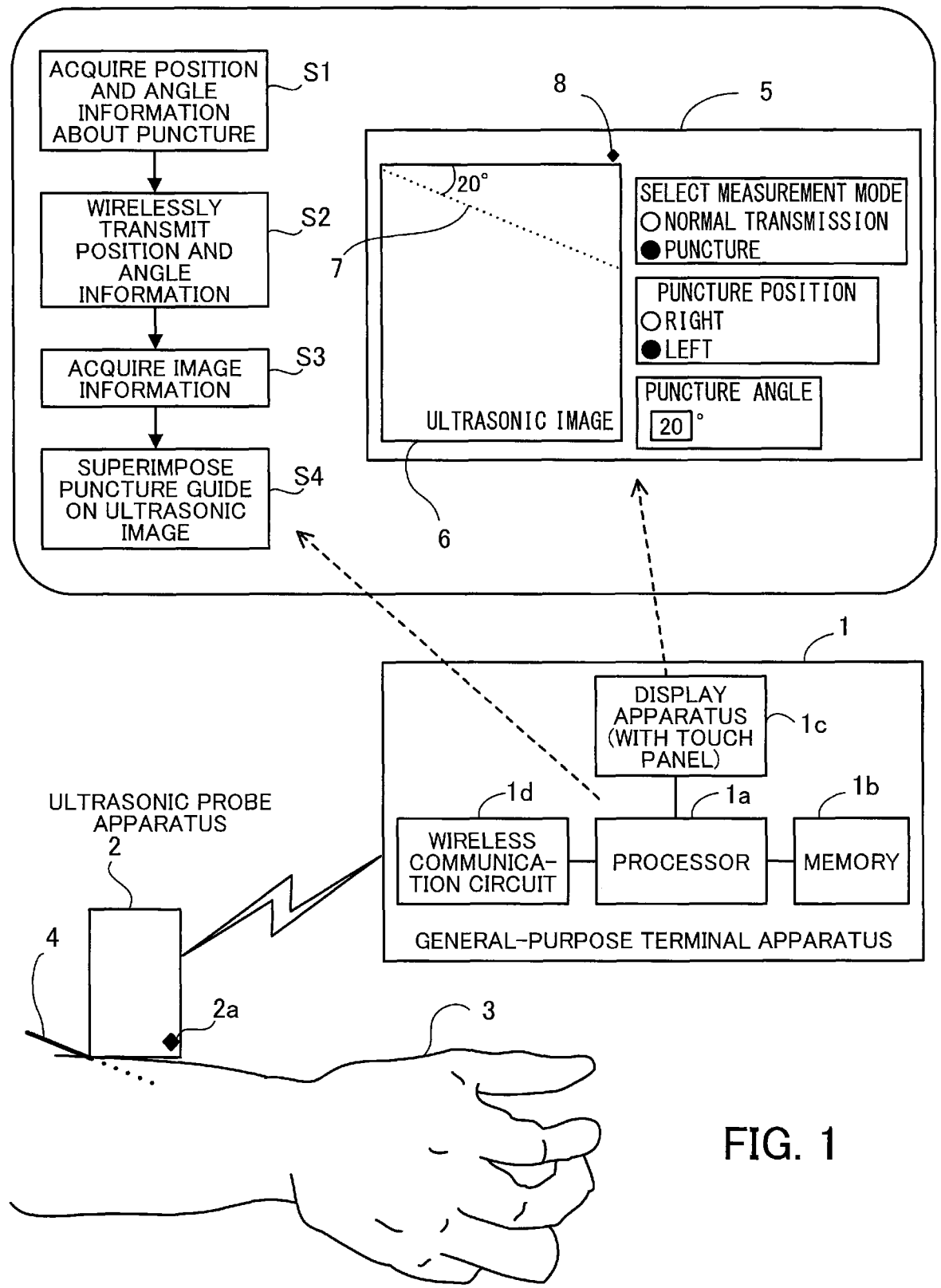
FIG. 1 illustrates an example of an ultrasonic probe control method according to a first embodiment.

Several embodiments will be described below with reference to the accompanying drawings, wherein like reference characters refer to like elements throughout.

First Embodiment

FIG. 1 illustrates an example of an ultrasonic probe control method according to a first embodiment.

The ultrasonic probe control method according to the first embodiment is performed by, for example, a general-purpose terminal apparatus 1 as illustrated in FIG. 1.

For example, the general-purpose terminal apparatus 1 is a tablet terminal apparatus, a smartphone, or the like and includes a processor 1a, a memory 1b, a display apparatus 1c having a touch panel, and a wireless communication circuit 1d.

The processor 1a performs steps S1 to S4 as illustrated in FIG. 1 on the basis of data and a program stored in the memory 1b. The processor 1a may be a multiprocessor. For example, the processor 1a is a central processing unit (CPU), a micro processing unit (MPU), a digital signal processor (DSP), an application specific integrated circuit (ASIC), or a programmable logic device (PLD). Alternatively, the processor 1a may be a combination of at least of two elements of a CPU, an MPU, a DSP, an ASIC, and a PLD.

The memory 1b holds a program executed by the processor 1a or various kinds of data. Any kind of storage device such as a flash memory or a solid state drive (SSD) may be used as the memory 1b.

The display apparatus 1c is, for example, a liquid crystal display, an organic electro-luminescence (OEL) display, or the like. Under control of the processor 1a, the display apparatus 1c displays an ultrasonic image, etc. on its screen. In addition, the display apparatus 1c has a touch panel, which receives instructions from a user (for example, a nurse, a clinician, or the like).

Under control of the processor 1a, the wireless communication circuit 1d wirelessly communicates with an ultrasonic probe apparatus 2.

The ultrasonic probe apparatus 2 receives information indicating puncture conditions (a puncture position and a puncture angle) wirelessly transmitted by the general-purpose terminal apparatus 1 and transmits ultrasonic waves of a plurality of channels at angles based on the information to a biological body 3 (for example, an arm of a patient as illustrated in FIG. 1). In addition, the ultrasonic probe apparatus 2 receives reflected waves according to the transmitted ultrasonic waves inside the biological body 3 and generates image information indicating the inside of the biological body 3 on the basis of the reflected waves. In addition, the ultrasonic probe apparatus 2 wirelessly transmits the generated image information to the general-purpose terminal apparatus 1.

A hardware configuration example of the ultrasonic probe apparatus 2 will be described below with reference to FIG. 2.

Hereinafter, an example of the ultrasonic probe control method performed when a user punctures the biological body 3 will be described.

For example, a screen 5 as illustrated in FIG. 1 is displayed on the display apparatus 1c. The user enters a measurement mode, a puncture position, and a puncture angle on the screen 5, which is a touch panel, with his or her finger, a stylus, or the like.

There are two measurement modes, which are a normal transmission mode for obtaining an ultrasonic image by focusing on tissue such as a blood vessel inside the biological body 3 and a puncture mode for obtaining an ultrasonic image by focusing on a needle 4 used for a puncture (hereinafter, a puncture needle 4). When the user performs a puncture, the user enters (selects) the puncture mode on the screen 5.

The user punctures the biological body 3 from a first side of the ultrasonic probe apparatus 2 or a second side opposite to the first side. Hereinafter, the first side will be considered to be the left side, and the second side will be considered to be the right side. The ultrasonic probe apparatus 2 has a marking 2a so that the user is able to recognize the right and left sides. In the example in FIG. 1, the ultrasonic probe apparatus 2 has the marking 2a on its right side. A marking 8 that corresponds to the marking 2a is displayed on the screen 5.

When the user punctures the biological body 3 from the left side of the ultrasonic probe apparatus 2, the user selects "left" as the puncture position. When the user punctures the biological body 3 from the right side of the ultrasonic probe apparatus 2, the user selects "right" as the puncture position. In this way, for example, the user is able to select a convenient puncture position on the basis of the dominant hand of the user or the positional relationship between the user and the biological body 3.

The user enters the puncture angle on the screen 5, for example, depending on which tissue inside the biological body 3 the end of the puncture needle 4 needs to be positioned at. For example, when the user touches a box in which a puncture angle is to be entered, a numeric keypad is displayed, and the user enters a puncture angle by touching the numeric keypad.

The processor 1a acquires information about the above puncture position entered on the touch panel as described above (hereinafter, position information) and the angle information indicating the puncture angle from the display apparatus 1c (step S1).

Next, the processor 1a wirelessly transmits the acquired position information and angle information to the ultrasonic probe apparatus 2 via the wireless communication circuit 1d (step S2).

When receiving the position information and the angle information, the ultrasonic probe apparatus 2 transmits ultrasonic waves at angles suitable for obtaining a clear ultrasonic image of the puncture needle 4 on the basis of the position information and the angle information. Next, the ultrasonic probe apparatus 2 generates image information on the basis of reflected waves according to the ultrasonic waves inside the biological body 3 and wirelessly transmits the image information to the general-purpose terminal apparatus 1.

To clearly display the puncture needle 4 when the user performs a puncture, it is desirable that ultrasonic waves be transmitted perpendicularly to the insertion direction of the puncture needle 4.

The processor 1a acquires the image information generated by the ultrasonic probe apparatus 2 via the wireless communication circuit 1d (step S3).

Next, the processor 1a superimposes a puncture guide indicating a puncture path based on the position information and the angle information on an ultrasonic image of the inside of the biological body 3 based on the acquired image information and displays the result of superimposing on the display apparatus 1c (step S4).

In the example in FIG. 1, a puncture guide 7 is superimposed on an ultrasonic image 6 and displayed on the screen 5. The puncture guide 7 is displayed at an angle of 20° from the top left corner of the ultrasonic image 6 in the downward right direction. While the puncture guide 7 is displayed in a dotted line in FIG. 1, for example, the display apparatus 1c may change the thickness, the color, or the kind of the line of the puncture guide 7, so that the user is able to view it easily.

The user punctures the biological body 3 with the puncture needle 4 along the puncture guide 7 while viewing the screen 5. Since the transmission angles of the ultrasonic waves are determined on the basis of the puncture position and the puncture angle, as long as the puncture needle 4 is inserted along the puncture guide 7, the puncture needle 4 is clearly displayed on the ultrasonic image 6. Thus, the user is able to easily see whether the puncture needle 4 is appropriately inserted into the biological body 3.

As described above, in the ultrasonic probe control method according to the present embodiment, the general-purpose terminal apparatus 1 wirelessly controls the ultrasonic probe apparatus 2 on the basis of the puncture conditions (the puncture position and the puncture angle) entered on the display apparatus 1c having a touch panel function. In addition, the general-purpose terminal apparatus 1 superimposes the puncture guide 7 based on the puncture conditions on the ultrasonic image 6 acquired by the ultrasonic probe apparatus 2 and displays the result of superimposing on the screen 5. In this way, the user is able to easily grasp the puncture state or set or change the puncture conditions on the screen 5 (the touch panel) of the general-purpose terminal apparatus 1. Namely, the user is able to perform a puncture operation easily.

In addition, the user is able to select the location of the general-purpose terminal apparatus 1 relatively freely, which is a tablet terminal apparatus, a smartphone, or the like. Thus, since the user is able to place the general-purpose terminal apparatus 1 at a convenient location when performing a puncture operation, the user has less burden on the puncture operation.

In addition, it is not a dedicated apparatus but the general-purpose terminal apparatus 1 that controls the ultrasonic probe apparatus 2. Thus, cost reduction is achieved.

Second Embodiment

Hereinafter, an ultrasonic probe control method according to a second embodiment will be described. The ultrasonic probe control methods according to the following embodiments will be described assuming that the general-purpose terminal apparatus 1 and the ultrasonic probe apparatus 2 as illustrated in FIG. 1 are used. For example, the ultrasonic probe apparatus 2 is realized by the following hardware configuration.

Figure 2:
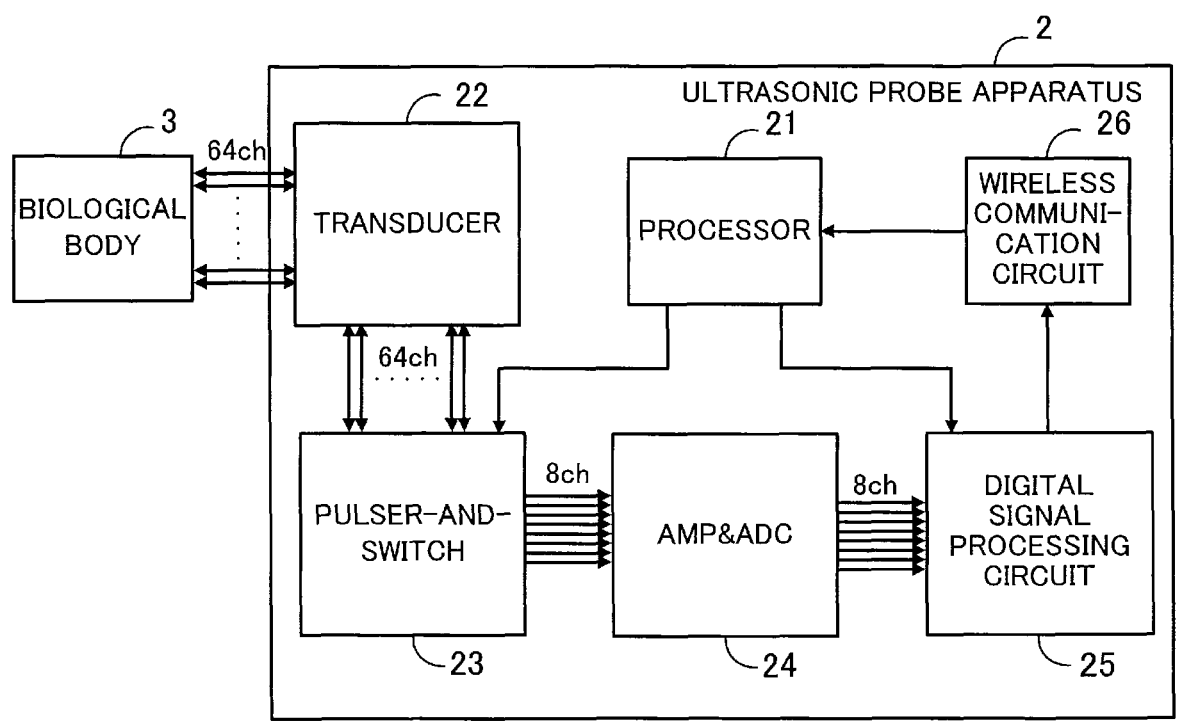
FIG. 2 illustrates a hardware configuration example of the ultrasonic probe apparatus.

FIG. 2 illustrates a hardware configuration example of the ultrasonic probe apparatus.

The ultrasonic probe apparatus 2 includes a processor 21, a transducer 22, a pulser-and-switch 23, an amplifier (AMP) &analogue-to-digital converter (ADC) 24, a digital signal processing circuit 25, and a wireless communication circuit 26.

The processor 21 controls the pulser-and-switch and the digital signal processing circuit 25, for example, on the basis of the information about the puncture position and the puncture angle received by the wireless communication circuit 26. The processor 21 is, for example, a CPU, an MPU, a DSP, an ASIC, or a PLD. Alternatively, the processor 21 may be a combination of at least two elements of a CPU, an MPU, a DSP, an ASIC, and a PLD. The ultrasonic probe apparatus 2 includes a memory (not illustrated) holding a program executed by the processor 21 or various kinds of data. Any kind of storage device such as a flash memory or an SSD may be used as the memory.

The transducer 22 transmits ultrasonic waves to the inside of the biological body 3 on the basis of the pulse signals generated by the pulser-and-switch 23. Inside the biological body 3, an individual ultrasonic wave is reflected at a border where the acoustic impedance changes, such as at a muscle, fat, or the puncture needle. The transducer 22 receives the reflected waves and outputs reception signals.

In the example in FIG. 2, 64 transmission and reception channels are set in a path between the transducer 22 and the biological body 3 and in a path between the transducer 22 and the pulser-and-switch 23. However, the number of channels set is not limited to 64. The channel spacing and the channel number determine the width and the resolution of the ultrasonic image to be captured.

The pulser-and-switch 23 outputs pulse signals having delay amounts each being different per channel under control of the processor 21, to adjust the focus of the ultrasonic waves simultaneously transmitted in the plurality of channels from the transducer 22 to the biological body 3.

In addition, among the 64 channels of reception signals outputted from the transducer 22, the pulser-and-switch 23 shifts eight channels per channel, selects the shifted channels, and outputs the channels to the AMP&ADC 24. The number of channels selected by the pulser-and-switch 23 is not limited to 8, either.

The AMP&ADC 24 amplifies the reception signals and converts the amplified signals into digital signals.

Under control of the processor 21, the digital signal processing circuit 25 generates and outputs image information indicating an ultrasonic image of the inside of the biological body 3 on the basis of the digital signals outputted from the AMP&ADC 24.

For example, the digital signal processing circuit 25 performs the timing adjustment on the eight channels of digital signals in view of the delay amounts of the pulse signals described above. Next, after performing averaging (phasing addition), the digital signal processing circuit 25 performs noise removal by using a digital filter and performs gain correction. Next, the digital signal processing circuit 25 performs envelope processing for extracting luminance information from the digital signals on which the gain correction has been performed. In addition, the digital signal processing circuit 25 performs thinning-out processing on the basis of the image resolution of the display apparatus 1c of the general-purpose terminal apparatus 1 and outputs luminance information (image information).

The wireless communication circuit 26 receives information about the puncture position and the puncture angle wirelessly transmitted from the general-purpose terminal apparatus 1. In addition, the wireless communication circuit 26 wirelessly transmits the image information, which has been outputted from the digital signal processing circuit 25, to the general-purpose terminal apparatus 1.

Hereinafter, an example of the ultrasonic probe control method according to the second embodiment in which the general-purpose terminal apparatus 1 illustrated in FIG. 1 and the ultrasonic probe apparatus 2 illustrated in FIG. 2 are used will be described.

Figure 3:
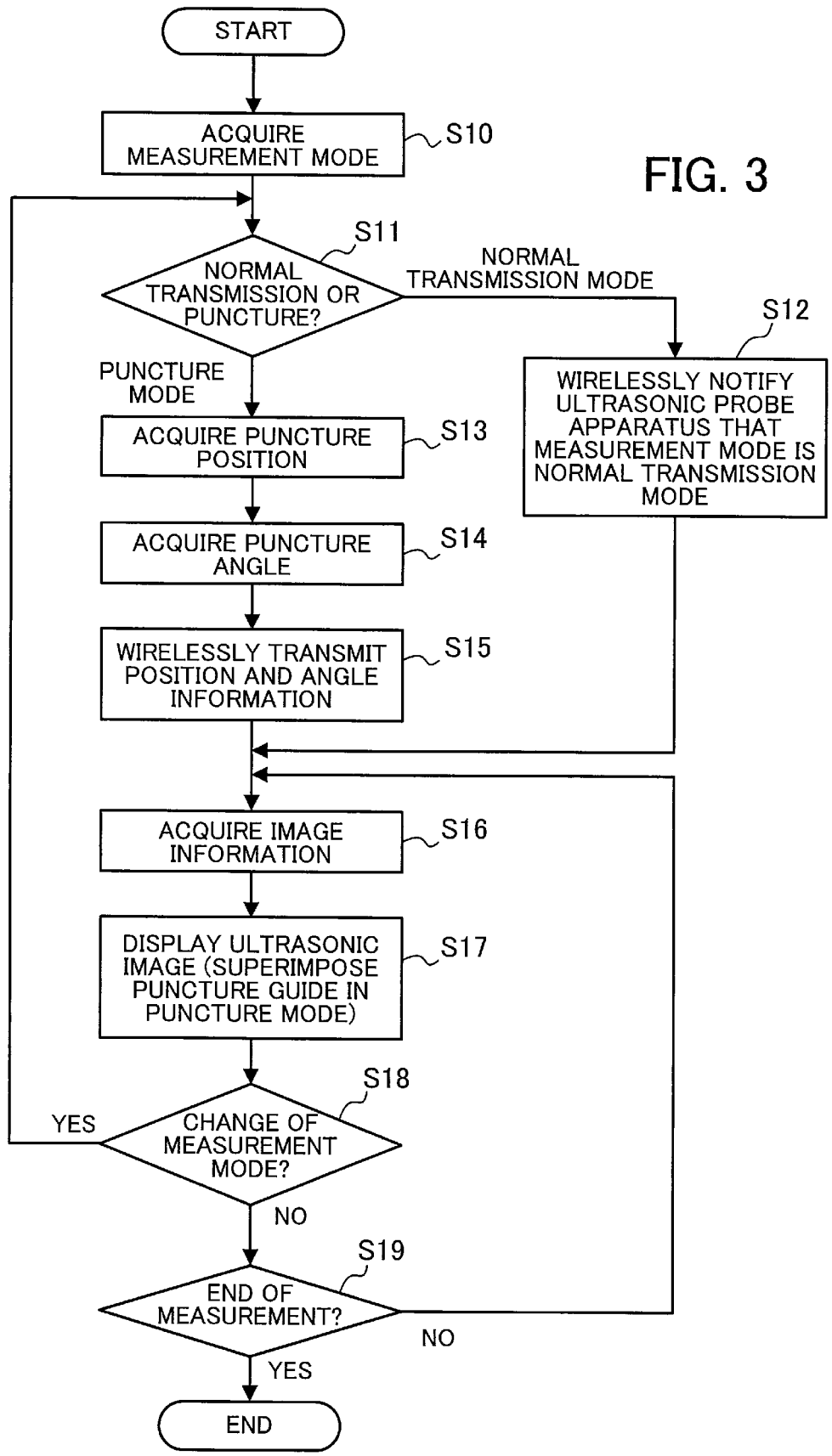
FIG. 3 is a flowchart illustrating an example of an ultrasonic probe control method according to a second embodiment.

FIG. 3 is a flowchart illustrating an example of the ultrasonic probe control method according to the second embodiment.

The processor 1a of the general-purpose terminal apparatus 1 acquires a measurement mode entered on the touch panel of the display apparatus 1c (step S10).

Next, the processor 1a determines whether the acquired measurement mode is the normal transmission mode or the puncture mode (step S11).

If the measurement mode is the normal transmission mode, under control of the processor 1a, the wireless communication circuit 1d wirelessly notifies the ultrasonic probe apparatus 2 that the measurement mode is the normal transmission mode (step S12). For example, when the user wishes to obtain an ultrasonic image in which tissue such as a blood vessel inside the biological body 3 is focused on, the user selects the normal transmission mode.

If the ultrasonic probe apparatus 2 is notified that the measurement mode is the normal transmission mode, for example, the ultrasonic probe apparatus 2 transmits ultrasonic waves as follows.

Figure 4:
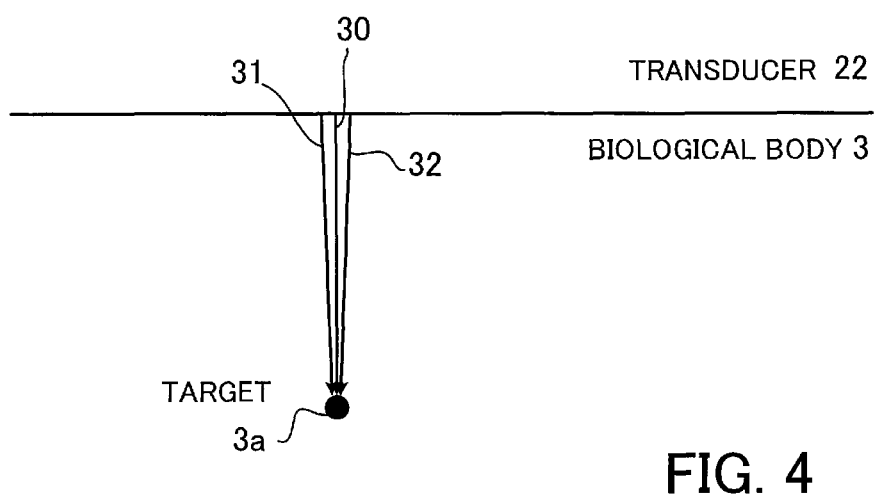
FIG. 4 illustrates an example of transmission of ultrasonic waves in a normal transmission mode.

FIG. 4 illustrates an example of transmission of ultrasonic waves in the normal transmission mode.

FIG. 4 simply illustrates an example of signals (ultrasonic waves) 30 to 32 that have been transmitted from three channels of the transducer 22. For example, as illustrated in FIG. 4, in the normal transmission mode, the delay amounts of the pulse signals are set so that a target 3a right under the transducer 22 is focused on. On the basis of the pulse signals, the transmission angles of the signals 30 to 32 transmitted from the transducer 22 are determined.

When the transducer 22 receives reflected waves, the above units of the ultrasonic probe apparatus 2 perform their respective processing. As a result, image information is generated and is wirelessly transmitted.

The processor 1a of the general-purpose terminal apparatus 1 acquires the image information via the wireless communication circuit 1d (step S16) and displays an ultrasonic image based on the acquired image information on the display apparatus 1c (step S17).

Figure 5:
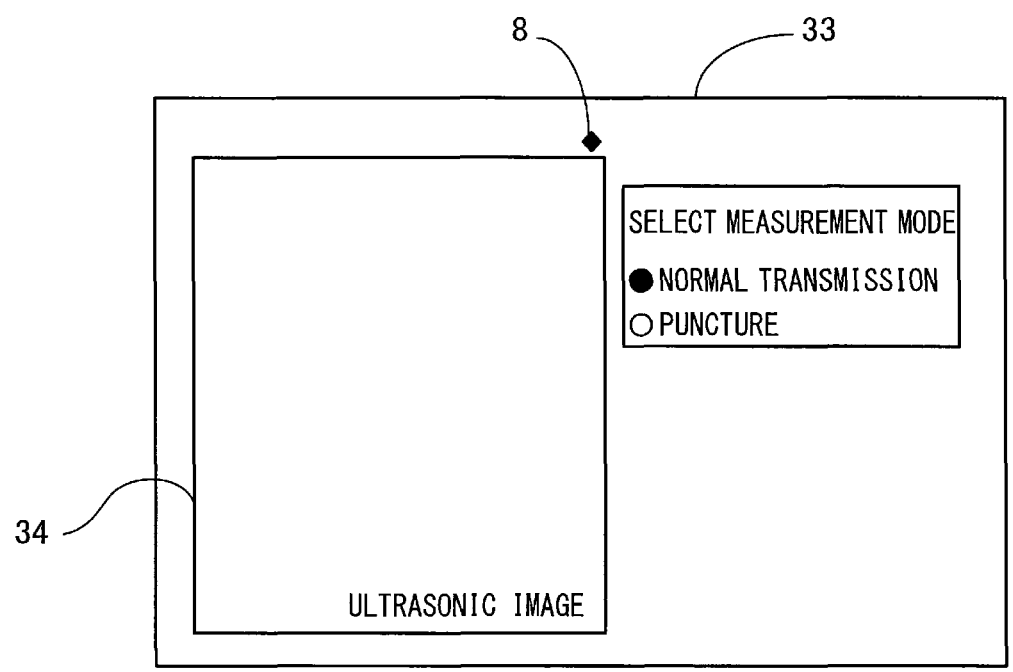
FIG. 5 illustrates an example of a screen displayed on a display apparatus in the normal transmission mode.

FIG. 5 illustrates an example of a screen displayed on the display apparatus in the normal transmission mode.

FIG. 5 illustrates an example in which the normal transmission mode has been selected on a screen 33 and an ultrasonic image 34 has been displayed in the normal transmission mode.

The processor 1a determines whether the measurement mode has been changed (step S18). If the measurement mode has been changed, the processing returns to step S11.

If the measurement mode has not been changed, the processor 1a determines whether the end of the measurement has been instructed (step S19). If the end of the measurement has been instructed, the processing proceeds to END. If not, the processing returns to step S16.

For example, the processor 1a causes the display apparatus 1c to display an end button on the touch panel thereof. If the user touches the end button, the processor 1a determines that the end of the measurement has been instructed.

In step S11, if the processor 1a determines that the acquired measurement mode is the puncture mode, the processor 1a acquires the puncture position and the puncture angle entered on the screen of the display apparatus 1c (steps S13 and S14). Next, the processor 1a wirelessly transmits the position information indicating the puncture position and the angle information indicating the puncture angle to the ultrasonic probe apparatus 2 via the wireless communication circuit 1d (step S15).

The processor 1a may calculate, from the acquired puncture position and puncture angle, the transmission angles of the ultrasonic waves so that the puncture needle 4 is focused on (so that the ultrasonic waves are transmitted perpendicularly to the puncture needle 4) and may transmit information indicating the transmission angles via the wireless communication circuit 1d.

When the ultrasonic probe apparatus 2 receives the position information indicating the puncture position and the angle information indicating the puncture angle (or the information indicating the transmission angles), for example, the ultrasonic probe apparatus 2 transmits ultrasonic waves to the biological body 3 as follows.

Figure 6:
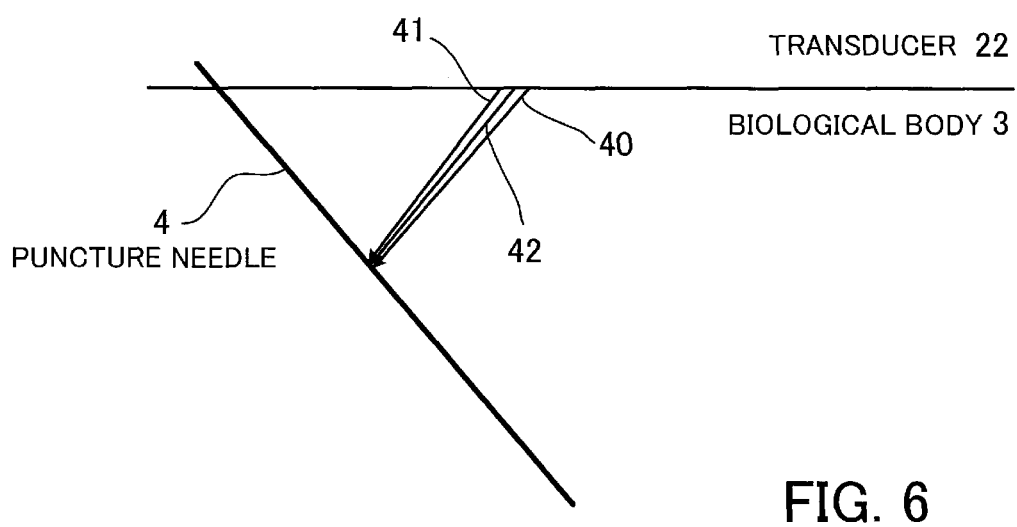
FIG. 6 illustrates an example of transmission of ultrasonic waves in a puncture mode.

FIG. 6 illustrates an example of transmission of ultrasonic waves in the puncture mode.

As in FIG. 4, FIG. 6 simply illustrates an example of signals (ultrasonic waves) 40 to 42 that have been transmitted from three channels of the transducer 22. For example, as illustrated in FIG. 6, in the puncture mode, the delay amounts of the pulse signals are set so that the puncture needle 4 inserted at the specified puncture position and puncture angle is focused on, and the transmission angles of the signals 40 to 42 transmitted from the transducer 22 are determined on the basis of the pulse signals.

When the transducer 22 receives reflected waves, the above units of the ultrasonic probe apparatus 2 perform their respective processing. As a result, image information is generated and is wirelessly transmitted. Next, the general-purpose terminal apparatus 1 performs the above steps S16 and S17.

In the puncture mode, a puncture guide is superimposed on the ultrasonic image.

Figure 7:
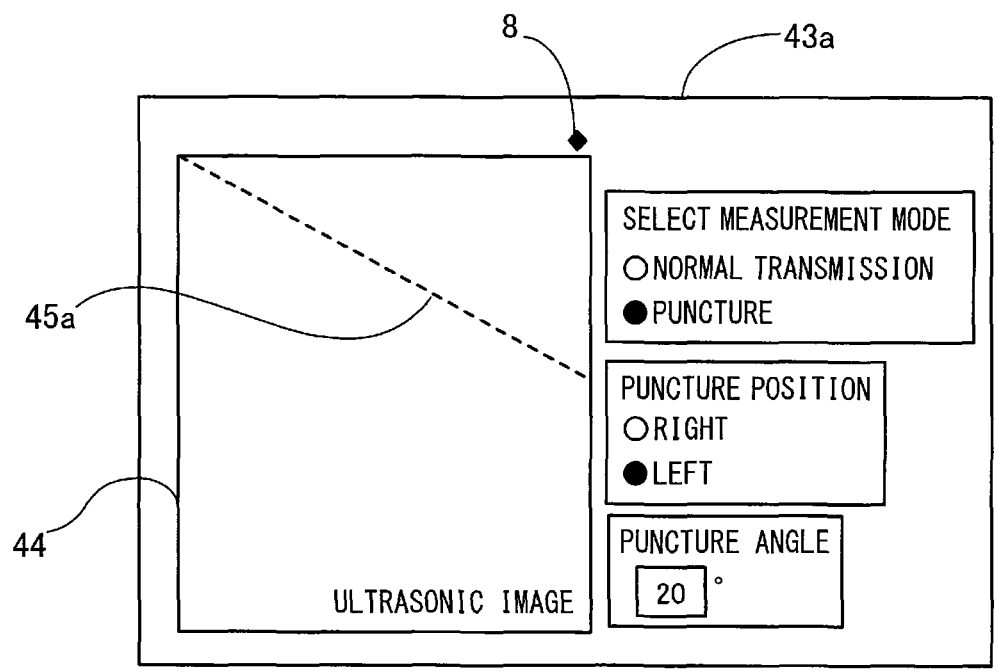
FIG. 7 illustrates an example of a screen displayed on a display apparatus in the puncture mode.

FIG. 7 illustrates an example of a screen displayed on the display apparatus in the puncture mode.

In the example in FIG. 7, the puncture mode has been selected as the measurement mode on a screen 43a, "left" has been selected as the puncture position, and 20° has been entered as the puncture angle. In this case, a puncture guide 45a that matches the above puncture position and puncture angle and that extends from the top left corner of the ultrasonic image 44 in the downward right direction is superimposed on an ultrasonic image 44 in the puncture mode and displayed on the screen 43a.

Figure 8:
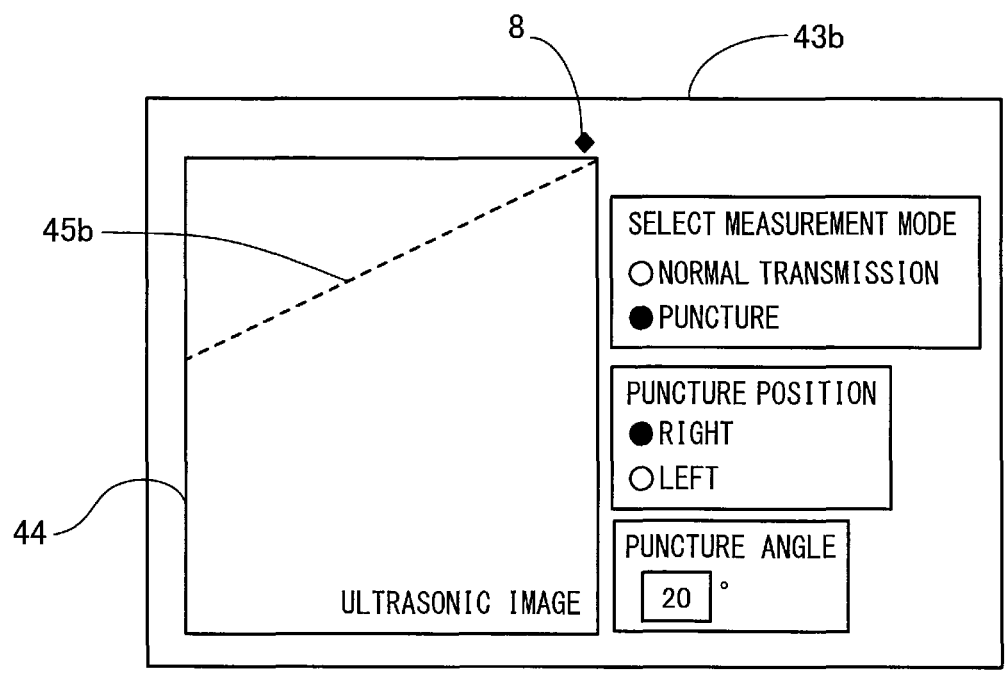
FIG. 8 illustrates another example of the screen displayed on the display apparatus in the puncture mode.

FIG. 8 illustrates another example of the screen displayed on the display apparatus in the puncture mode.

In the example in FIG. 8, on a screen 43b, the puncture mode has been selected as the measurement mode, "right" has been selected as the puncture position, and 20° has been entered as the puncture angle. In this case, a puncture guide 45b that matches the above puncture position and puncture angle and that extends from the top right corner of the ultrasonic image 44 in the downward left direction is superimposed on the ultrasonic image 44 in the puncture mode and displayed on the screen 43b.

The user inserts the puncture needle 4 into the biological body 3 along the above puncture guide 45a or 45b while viewing the screen 43a or 43b. In this way, the user is able to perform the puncture accurately and easily. The user may be allowed to slide the puncture guide 45a or 45b to a desired position on the touch panel.

The ultrasonic probe control method according to the second embodiment provides advantageous effects equivalent to those provided by the ultrasonic probe control method according to the first embodiment. In addition, the user is able to easily switch the normal transmission mode and the puncture mode on the screen (the touch panel) of the display apparatus 1c of the general-purpose terminal apparatus 1 and easily switch to an ultrasonic image suitable for the content set on the screen.

The steps illustrated in FIG. 3 may be performed in a different sequence. For example, the processor 1a may cause the display apparatus 1c to display an ultrasonic image in the normal transmission mode first and may allow the user to shift the measurement mode to the puncture mode next.

Third Embodiment

Hereinafter, an ultrasonic probe control method according to a third embodiment will be described.

Figure 9:
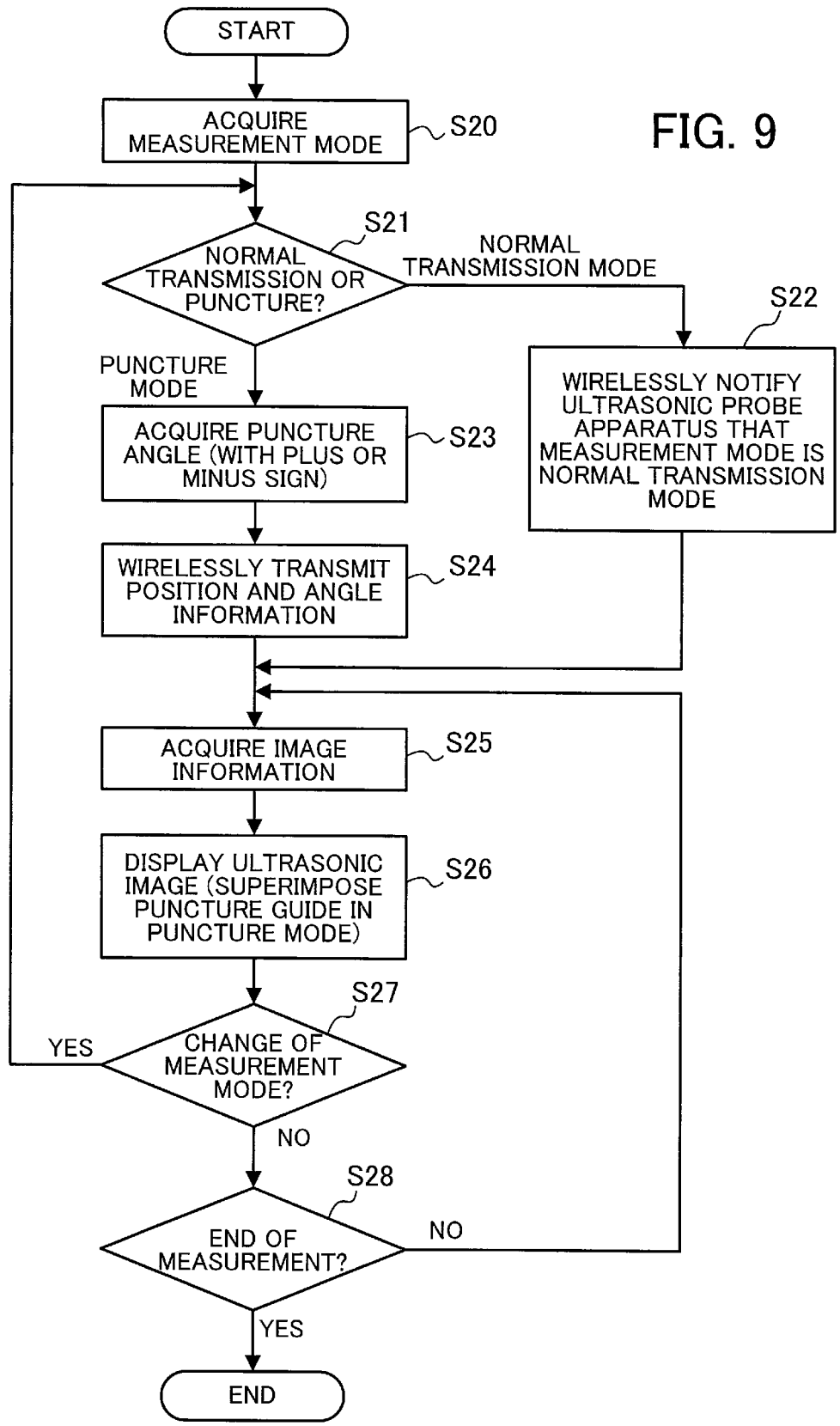
FIG. 9 is a flowchart illustrating an example of an ultrasonic probe control method according to a third embodiment.

FIG. 9 is a flowchart illustrating an example of the ultrasonic probe control method according to the third embodiment.

Steps S20 to S22 are the same as steps S10 to S12 illustrated in FIG. 3.

In the ultrasonic probe control method according to the third embodiment, in the puncture mode, the processor 1a acquires a puncture angle (with a plus or minus sign) entered on the touch panel of the display apparatus 1c (step S23).

The sign added to the puncture angle indicates the puncture position. For example, when a puncture is performed from the left side of the ultrasonic probe apparatus 2 (when the puncture position is "left"), the plus sign is added to the puncture angle. When a puncture is performed from the right side of the ultrasonic probe apparatus 2 (when the puncture position is "right"), the minus sign is added to the puncture angle.

Next, the processor 1a transmits the position information indicating the puncture position expressed by the above sign and the angle information indicating the puncture angle to the ultrasonic probe apparatus 2 via the wireless communication circuit 1d (step S24). The subsequent steps S25 to S28 are the same as steps S16 to S19 in FIG. 3.

Figure 10:
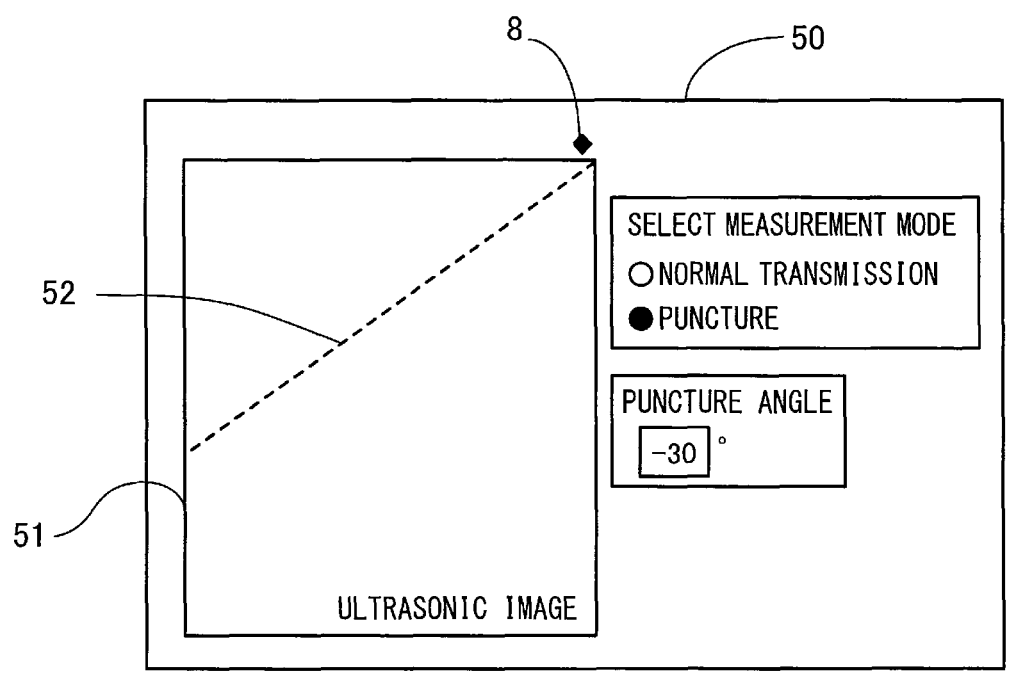
FIG. 10 illustrates an example of a screen displayed on a display apparatus in the ultrasonic probe control method according to the third embodiment.

FIG. 10 illustrates an example of a screen displayed on the display apparatus in the ultrasonic probe control method according to the third embodiment.

In the example in FIG. 10, on a screen 50, the puncture mode has been selected as the measurement mode, and −30° has been entered as the puncture angle. In addition, "−" indicates that the puncture position is "right". In this case, a puncture guide 52 that matches the above puncture position and puncture angle and that extends from the top right corner of the ultrasonic image 44 in the downward left direction is superimposed on an ultrasonic image 51 in the puncture mode and displayed on the screen 50.

The ultrasonic probe control method according to the third embodiment also provides advantageous effects equivalent to those provided by the ultrasonic probe control method according to the second embodiment.

As in the ultrasonic probe control method according to the second embodiment, the steps illustrated in FIG. 9 may be performed in a different sequence.

Fourth Embodiment

Hereinafter, an ultrasonic probe control method according to a fourth embodiment will be described.

Figure 11:
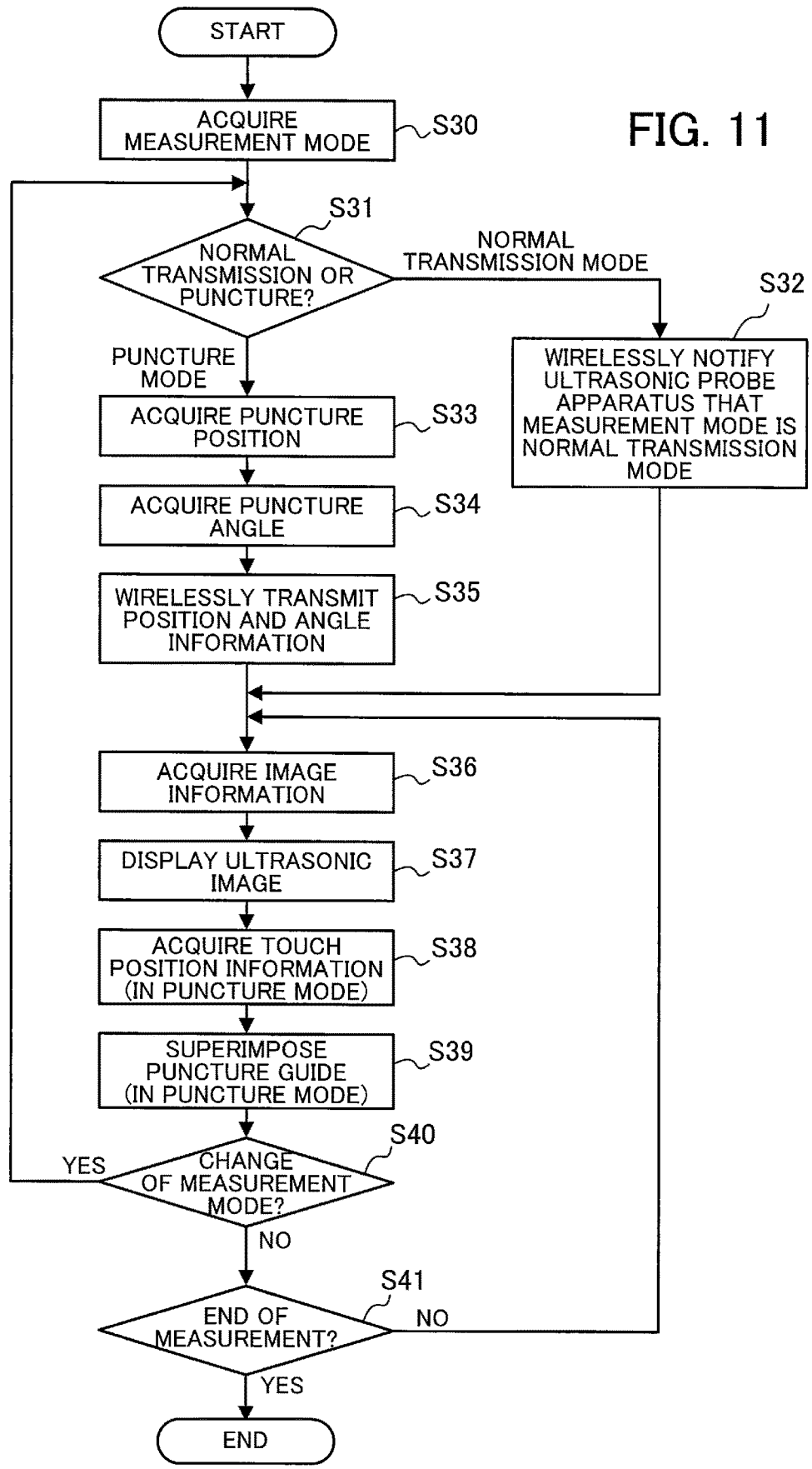
FIG. 11 is a flowchart illustrating an example of an ultrasonic probe control method according to a fourth embodiment.

FIG. 11 is a flowchart illustrating an example of the ultrasonic probe control method according to the fourth embodiment.

Step S30 to S36 are the same as steps S10 to S16 illustrated in FIG. 3.

In step S37, the processor 1a causes the display apparatus 1c to display an ultrasonic image on the basis of the acquired image information. Next, when the measurement mode is the puncture mode, the processor 1a acquires touch position information indicating a position touched by the user on the screen (the touch panel) of the display apparatus 1c (step S38).

In addition, when the measurement mode is the puncture mode, the processor 1a superimposes the puncture guide displayed by using the touch position as a start point or an end point on the ultrasonic image and displays the result of superimposing on the display apparatus 1c, on the basis of the touch position information, the position information indicating the puncture position, and the angle information indicating the puncture angle (step S39).

Figure 12:
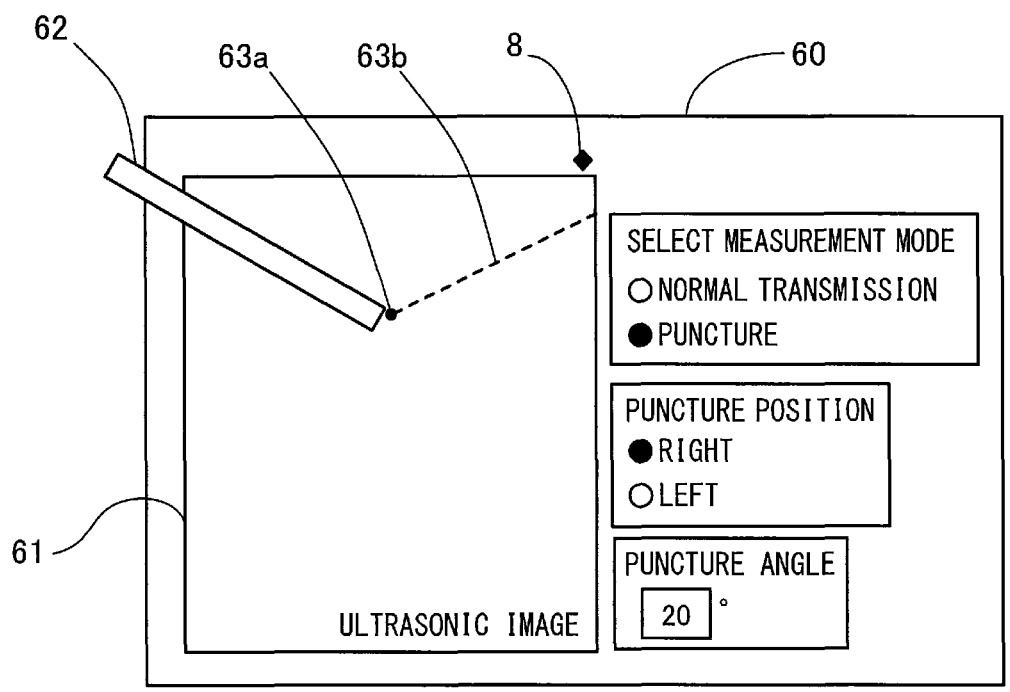
FIG. 12 illustrates a setting example of a puncture guide in the ultrasonic probe control method according to the fourth embodiment.

FIG. 12 illustrates a setting example of the puncture guide in the ultrasonic probe control method according to the fourth embodiment.

In the example in FIG. 12, on a screen 60, the puncture mode has been selected as the measurement mode, "right" has been selected as the puncture position, and 20° has been entered as the puncture angle. When a certain position (for example, a position where a target that the user wishes to puncture is displayed) on an ultrasonic image 61 displayed on the screen 60 is touched by a finger 62 or the like, the processor 1a acquires touch position information (for example, coordinates) indicating this position. Next, the processor 1a superimposes a puncture guide 63b extending in the upward right at an angle of 20° by using the position as the start point (or the end point) 63a on the ultrasonic image 61 and displays the result of superimposing on the display apparatus 1c.

Steps S40 and S41 are the same as steps S18 and S19 illustrated in FIG. 3.

The ultrasonic probe control method according to the fourth embodiment also provides advantageous effects equivalent to those provided by the ultrasonic probe control method according to the second embodiment. In addition, the present ultrasonic probe control method enables the user to perform a puncture operation on a target (tissue inside the biological body 3) more easily.

As in the ultrasonic probe control method according to the second embodiment, the steps illustrated in FIG. 11 may be performed in a different sequence.

Fifth Embodiment

Hereinafter, an ultrasonic probe control method according to a fifth embodiment will be described.

Figure 13:
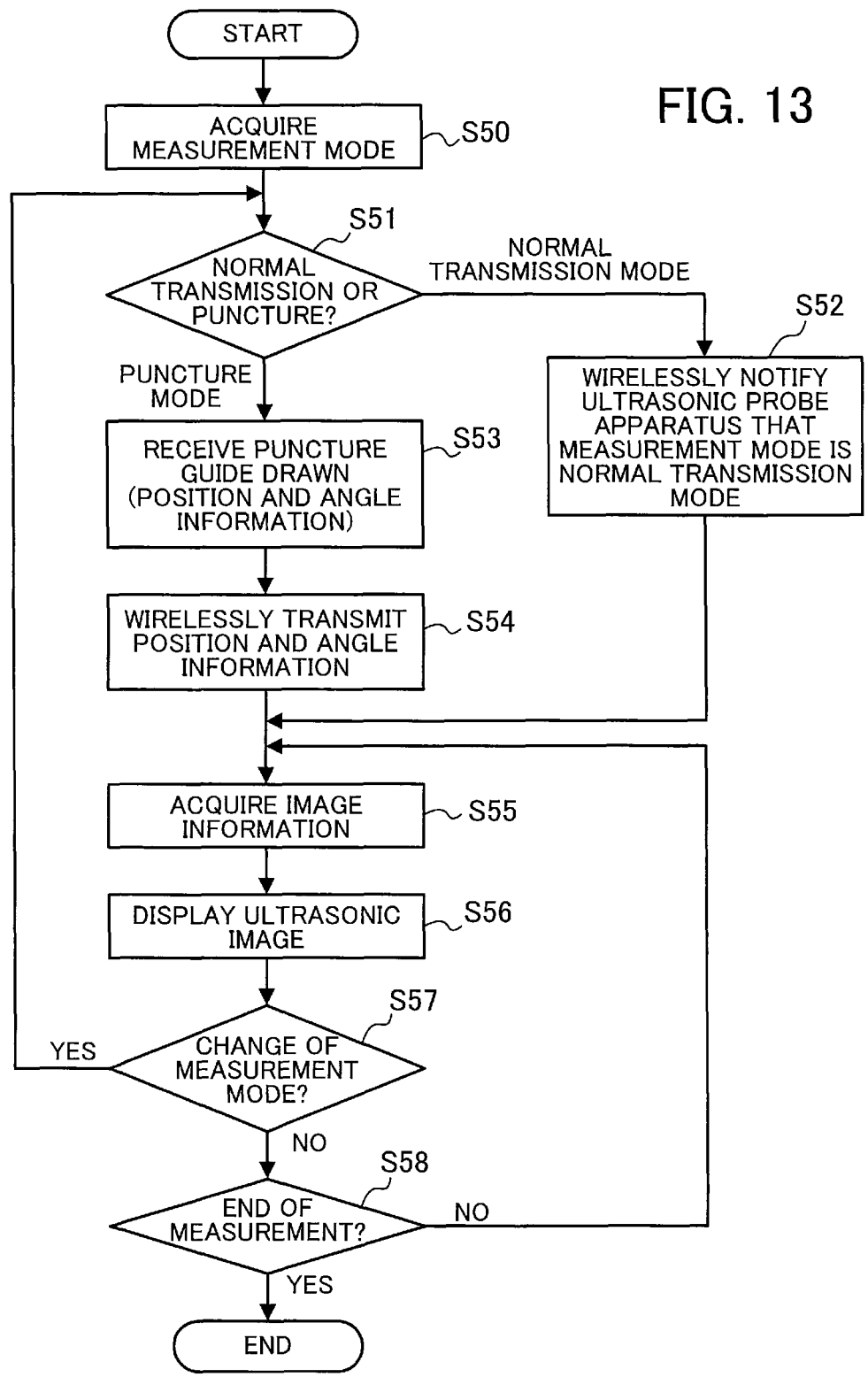
FIG. 13 is a flowchart illustrating an example of an ultrasonic probe control method according to a fifth embodiment.

FIG. 13 is a flowchart illustrating an example of the ultrasonic probe control method according to the fifth embodiment.

Steps S50 to S52 are the same as steps S10 to S12 illustrated in FIG. 3.

In step S53, the processor 1a receives a puncture guide drawn by the user on the touch panel of the display apparatus 1c. For example, in step S53, an ultrasonic image based on the image information acquired in the normal transmission mode is displayed on the screen of the display apparatus 1c, and the user draws a puncture guide having a desired angle while using a puncture target displayed on the ultrasonic image as the start point or the end point.

Figure 14:
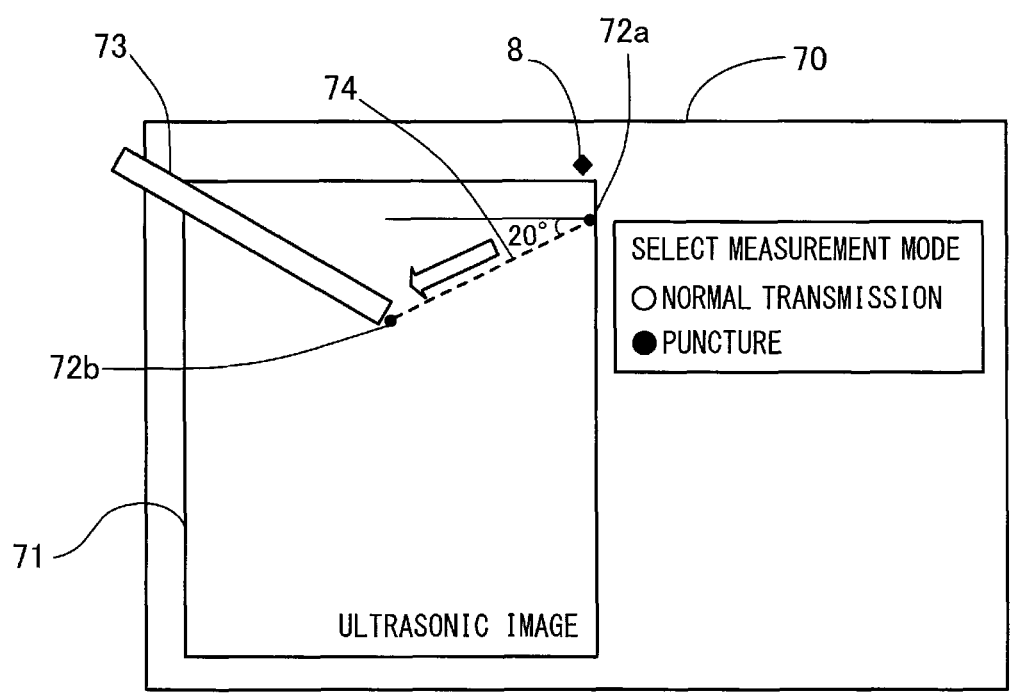
FIG. 14 illustrates a drawing example of a puncture guide in the ultrasonic probe control method according to the fifth embodiment.

FIG. 14 illustrates a drawing example of a puncture guide in the ultrasonic probe control method according to the fifth embodiment.

In example in FIG. 14, the puncture mode has been selected as the measurement mode. In addition, FIG. 14 illustrates an example of a puncture guide 74 drawn when the user runs his or her finger 73 or the like from a position 72a to a position 72b on an ultrasonic image 71 displayed on a screen 70, which is a touch panel.

In step S53, the processor 1a acquires position information (for example, coordinates) about the positions 72a and 72b as the position information indicating the puncture position and the angle information indicating the puncture angle. This is because the puncture position and the puncture angle are determined from the position information about the positions 72a and 72b. For example, when the puncture guide 74 is drawn as illustrated in FIG. 14, the puncture position is "right", and the puncture angle is 20°.

The processor 1a wirelessly transmits the position information and the angle information to the ultrasonic probe apparatus 2 via the wireless communication circuit 1d (step S54).

The subsequent steps S55 to S58 are the same as steps S16 to S19 illustrated in FIG. 3.

The processor 1a may superimpose the puncture guide 74 extending between the positions 72a and 72b illustrated in FIG. 14 on the ultrasonic image and displays the result of superimposing on the display apparatus 1C in step S56.

The ultrasonic probe control method according to the fifth embodiment also provides advantageous effects equivalent to those provided by the ultrasonic probe control method according to the first embodiment. In addition, the present ultrasonic probe control method enables the user to enter the puncture conditions (puncture position and puncture angle) more easily.

As in the ultrasonic probe control method according to the second embodiment, the steps illustrated in FIG. 13 may be performed in a different sequence.

As described above, the ultrasonic probe control methods according to the above embodiments may be realized by causing the general-purpose terminal apparatus 1 as a computer to execute programs. Each of these programs may be stored in a computer-readable storage medium.

For example, a magnetic disk, an optical disc, a magneto-optical disk, a semiconductor memory, or the like may be used as the storage medium. Examples of the magnetic disk include a hard disk drive (HDD), and examples of the optical disc include a compact disc read-only memory (CD-ROM), a CD-Recordable (R)/Rewritable (RW), a digital versatile disc (DVD), and a DVD-random access memory (RAM).

When any one of the programs is distributed, for example, a portable storage medium in which the program is stored is provided. The program may be stored in a storage device of another computer and be distributed via a network.

For example, a computer may store the program stored in a portable storage medium or received from another computer in a storage device (for example, the memory 1b), read the program from the storage device, and execute the read program. Alternatively, the computer may directly execute the program read from the portable storage medium or directly execute the program received from another computer via a network.

According to the ultrasonic probe control methods and the programs described above, users are able to perform puncture operations easily.

All examples and conditional language provided herein are intended for the pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that various changes, substitutions, and alterations could be made hereto without departing from the spirit and scope of the invention.

What is claimed is:

1. An ultrasonic probe control method comprising:
   receiving before a biological body is punctured by a puncture needle from a display apparatus, which has a touch panel, of a general-purpose terminal apparatus, by a processor of the general-purpose terminal apparatus, position information which indicates whether the biological body is punctured from a first side of an ultrasonic probe apparatus or a second side opposite to the first side and an angle information which indicates a puncture angle, the position information and the angle information being entered on the touch panel;
   transmitting, by the processor, the position information and the angle information to the ultrasonic probe apparatus, which has a function to transmit a first ultrasonic wave at a first angle for obtaining a first ultrasonic image by focusing on the puncture needle based on the position information and the angle information, via a wireless communication circuit of the general-purpose terminal apparatus;
   acquiring, by the processor, via the wireless communication circuit, first image information of the first ultrasonic image generated and transmitted by the ultrasonic probe apparatus based on a first reflected wave obtained by transmitting the first ultrasonic wave into the biological body from the ultrasonic probe apparatus at the first angle; and
   superimposing before the biological body is punctured by the puncture needle, by the processor, a puncture guide, which indicates a puncture path and is acquired based on the position information and the angle information, on the first ultrasonic image based on the first image information and displaying a result of the superimposing on the display apparatus.

2. The ultrasonic probe control method according to claim 1,
   wherein the processor determines which of measurement modes has been selected on the touch panel, a first measurement mode for obtaining the first ultrasonic image or a second measurement mode for obtaining a second ultrasonic image in which tissue inside the biological body is focused on,
   wherein, when the processor determines that the first measurement mode has been selected, the processor acquires the position information and the angle information, transmits the position information and the angle information to the ultrasonic probe apparatus via the wireless communication circuit, acquires the first image information, superimposes the puncture guide on the first ultrasonic image, and displays a result of the superimposing on the display apparatus, and
   wherein, when the processor determines that the second measurement mode has been selected, the processor notifies the ultrasonic probe apparatus that the second measurement mode has been selected via the wireless communication circuit, acquires, via the wireless communication circuit, second image information generated and transmitted by the ultrasonic probe apparatus based on a second reflected wave obtained by transmitting a second ultrasonic wave into the biological body from the ultrasonic probe apparatus at a second angle, and displays a second ultrasonic image of the biological body based on the second image information on the display apparatus.

3. The ultrasonic probe control method according to claim 1,
   wherein the processor acquires touch position information which indicates a position touched by a user on the touch panel displaying the first ultrasonic image, and
   wherein the processor superimposes, based on the touch position information, the position information, and the angle information, the puncture guide using the position as a start point or an end point on the first ultrasonic image and displays a result of the superimposing on the display apparatus.

4. The ultrasonic probe control method according to claim 1, wherein, when a user traces a line from a first position to a second position on the touch panel, the position information is determined from a relationship between coordinates of the first position and coordinates of the second position and the angle information is determined from an angle of the line from an axis in a first direction of the touch panel.

5. A non-transitory computer-readable storage medium storing a computer program that causes a computer to perform a procedure comprising:

receiving before a biological body is punctured by a puncture needle from a display apparatus, which has a touch panel, of a general-purpose terminal apparatus, position information which indicates whether the biological body is punctured from a first side of an ultrasonic probe apparatus or a second side opposite to the first side and an angle information which indicates a puncture angle, the position information and the angle information being entered on the touch panel;

transmitting the position information and the angle information to the ultrasonic probe apparatus, which has a function to transmit a first ultrasonic wave at a first angle for obtaining a first ultrasonic image by focusing on the puncture needle based on the position information and the angle information, via a wireless communication circuit;

acquiring, via the wireless communication circuit, first image information of the first ultrasonic image generated and transmitted by the ultrasonic probe apparatus based on a first reflected wave obtained by transmitting the first ultrasonic wave into the biological body from the ultrasonic probe apparatus at the first angle; and superimposing before the biological body is punctured by the puncture needle, a puncture guide, which indicates a puncture path and is acquired based on the position information and the angle information, on the first ultrasonic image based on the first image information and displaying a result of the superimposing on the display apparatus.

\* \* \* \* \*